(12) United States Patent
Mees et al.

(10) Patent No.: US 6,906,233 B2
(45) Date of Patent: Jun. 14, 2005

(54) MODIFIED METALLOALUMINOPHOSPHATE MOLECULAR SIEVES

(75) Inventors: Filip Mees, Grobbendonk (BE); Etienne Vansant, Zoersel (BE); Kun Wang, Bridgewater, NJ (US); Richard B. Hall, Whitehouse Station, NJ (US); Marcel Johannes Janssen, Kessel-Lo (BE); Luc Roger Marc Martens, Meise (BE); An Amandine Verberckmoes, Serskamp (BE); Guang Cao, Branchburg, NJ (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/317,425

(22) Filed: Dec. 12, 2002

(65) Prior Publication Data

US 2004/0116282 A1 Jun. 17, 2004

(51) Int. Cl.$^7$ ................................................ C07C 1/00
(52) U.S. Cl. .................... 585/640; 585/638; 585/639
(58) Field of Search ................................ 585/638, 639, 585/640

(56) References Cited

U.S. PATENT DOCUMENTS

| | | | |
|---|---|---|---|
| 3,911,041 A | 10/1975 | Kaeding et al. | ............ 260/682 |
| 3,979,472 A | 9/1976 | Butter | ........................ 260/668 |
| 4,088,706 A | 5/1978 | Kaeding | ...................... 260/668 |
| 4,159,282 A | 6/1979 | Olson et al. | ................. 585/481 |
| 4,414,005 A * | 11/1983 | De Bievre et al. | ............ 95/127 |
| 4,471,150 A | 9/1984 | Wu | ............................ 585/640 |
| 4,499,327 A | 2/1985 | Kaiser | ........................ 585/640 |
| 4,752,596 A | 6/1988 | Bergna et al. | ................ 502/64 |
| 4,933,162 A | 6/1990 | Vansant et al. | ............. 423/488 |
| 5,000,931 A | 3/1991 | Gortsema et al. | ........... 423/305 |
| 5,003,120 A | 3/1991 | Newman et al. | ............ 585/323 |
| 5,145,816 A | 9/1992 | Beck et al. | ................... 502/60 |
| 5,250,484 A | 10/1993 | Beck et al. | ................... 502/71 |
| 5,981,418 A | 11/1999 | Drake et al. | ................. 502/64 |
| 6,046,371 A | 4/2000 | Wu et al. | .................... 585/638 |
| 6,046,372 A * | 4/2000 | Brown et al. | ............... 585/640 |
| 6,080,901 A | 6/2000 | Drake et al. | ................ 585/407 |
| 6,107,534 A | 8/2000 | Drake et al. | ................ 585/411 |
| 6,114,268 A | 9/2000 | Wu et al. | ..................... 502/74 |
| 6,156,689 A | 12/2000 | Kimble et al. | ................ 502/77 |
| 6,372,680 B1 | 4/2002 | Wu et al. | ..................... 502/64 |
| 6,472,569 B1 | 10/2002 | Wu et al. | ................... 568/698 |
| 2002/0183577 A1 * | 12/2002 | Haw et al. | ................... 585/639 |

FOREIGN PATENT DOCUMENTS

| | | | |
|---|---|---|---|
| WO | WO 97/26989 | 7/1997 | ............ B01J/29/04 |
| WO | WO 98/15496 | 7/1998 | ........... C01B/25/45 |
| WO | WO 00/63144 | 10/2000 | ........... C07C/41/09 |
| WO | WO 02/070407 | 9/2002 | ........... C01B/37/08 |
| WO | WO 02/085514 | 10/2002 | ............ B01J/29/00 |

OTHER PUBLICATIONS

Dahl, I. M. et al., *Catal. Lett.*, vol. 20, pp. 329–336 (1993).
Dahl, I. M. et al., *J. Catal.*, vol. 149, pp. 458–464 (1994).
Dahl, I. M. et al., *J. Catal.* vol. 161, pp. 304–309 (1996).
Goguen, P.W. et al.,*J. Am. Chem. Soc.*, vol. 120, pp. 2650–2651 (1998).
Song et al., *J. Am. Chem. Soc.*, vol. 122, pp. 10726–10727 (2000).
Song et al., *J. Am. Chem. Soc.*, vol. 123, pp. 4749–4754 (2001).
Song et al., *J. Phys. Chem.*, B, vol. 105, pp. 12839–12843 (2001).
Arstad, B. et al., *Catal. Lett.*, vol. 71, pp. 209–212 (2001).
Arstad, B., et al. *J. Am. Chem. Soc.*, vol. 123, pp. 8137–8138 (2001).
Komiya et al., *Sekyiyu Gakkaishi*, vol. 28 (3), pp. 257–263 (1985).
Geimar et al., *Fortschr. Miner.*, vol. 65(1), pp. 115–128 (1987).
Wilson, S. T., et al., *Microporous and Mesoporous Materials*, vol. 28, pp. 125–137 (1999).

* cited by examiner

*Primary Examiner*—Christina Johnson

(57) ABSTRACT

The invention is directed to a method for modifying a microporous metalloaluminophosphate molecular sieve, the method comprising the steps of a) introducing a compound containing at least one M-X group within the cages of said microporous molecular sieve; and b) reacting said compound containing at least one M-X group with the acid groups located in the cages of the molecular sieve, wherein the compound containing at least one M-X group is selected from the group consisting of compounds of formula $MX_3$, compounds of formula $M_2X_6$, and mixtures thereof, M being a metal belonging to Group 13 of the Periodic Table, and each X independently being a hydrogen or halogen atom. Preferably, X is a hydrogen atom. The present invention also relates to modified metalloaluminophosphate molecular sieves, preferably modified silicoaluminophosphate molecular sieves, as well as to the use of these modified molecular sieves in catalytic processes, such as processes for the conversion of oxygenated hydrocarbon feedstocks.

6 Claims, 5 Drawing Sheets

MODIFIED METALLOALUMINOPHOSPHATE MOLECULAR SIEVES

FIELD OF INVENTION

The present invention relates to modified metalloaluminophosphate molecular sieves, preferably modified silicoaluminophosphate molecular sieves, as well as to methods of preparing these modified molecular sieves. The present invention also relates to the use of these modified molecular sieves in catalytic processes, such as processes for the conversion of oxygenated hydrocarbon feedstocks.

BACKGROUND OF THE INVENTION

Olefins, particularly light olefins, have been traditionally produced from petroleum feedstocks by either catalytic or steam cracking. Oxygenates, however, are becoming an alternative feedstock for making light olefins, particularly ethylene and propylene. Promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including natural gas. Because of the relatively low-cost of these sources, alcohol, alcohol derivatives, and other oxygenates have promise as an economical source for light olefin production.

One way of producing olefins is by the conversion of methanol to olefins (MTO) catalyzed by a molecular sieve. Useful molecular sieves for converting methanol to olefin(s) are non-zeolitic molecular sieves, in particular metalloaluminophosphates such as the silicoaluminophosphates (SAPO's). For example, U.S. Pat. No. 4,499,327 to Kaiser, fully incorporated herein by reference, discloses making olefins from methanol using a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 $hr^{-1}$. Crystalline aluminosilicate zeolites have also been reported as catalysts for converting methanol and/or dimethyl ether to olefin-containing hydrocarbon mixtures. For example, U.S. Pat. No. 3,911,041 discloses that methanol can be converted to C2–C4 olefins by contacting the methanol at a temperature of 300° C. to 700° C. with a crystalline aluminosilicate zeolite catalyst which has a Constraint Index of 1–12, such as ZSM-5, and which contains at least 0.78% by weight of phosphorus incorporated in the crystal structure of the zeolite.

Zeolitic aluminosilicate molecular sieves contain a three-dimensional microporous crystal framework structure of $[SiO_2]$ and $[AlO_2]$ corner sharing tetrahedral units. Metalloaluminophosphate (MeAPO) molecular sieves, often qualified as non-zeolitic molecular sieves, contain a three-dimensional microporous crystal framework structure of $[MO_2]$, $[AlO_2]$ and $[PO_2]$ corner sharing tetrahedral units. When M is silicon, the molecular sieves are referred to as silicoaluminophosphate (SAPO) molecular sieves. There are a wide variety of aluminosilicate and MeAPO molecular sieves known in the art. Of these the more important examples as catalysts for the conversion of oxygenates to olefins include ZSM-5, ZK-5, ZSM-11, ZSM-12, ZSM-34, ZSM-35, erionite, chabazite, offretite, silicalite and other similar materials, SAPO-5, SAPO-11, SAPO-17, SAPO-18, SAPO-34, SAPO-35, SAPO-41, SAPO-56 and other similar materials. SAPO molecular sieves having the CHA framework type and especially SAPO-34 are particularly important catalysts. Another important class of SAPO molecular sieves consists of mixed or intergrown phases of molecular sieves having the CHA and AEI framework types. Examples of such materials are disclosed in WO 98/15496, published 16 Apr. 1998, and in WO 02/070407, published Sep. 12, 2002, both herein fully incorporated by reference.

While the aforementioned molecular sieves exhibit good catalytic properties in the conversion of methanol to olefins, there remains a need to improve their catalytic performance in order to decrease their selectivity to undesired saturated hydrocarbons and to increase their selectivity to desired light olefins (ethylene and propylene).

Various methods have been reported for treating and/or modifying crystalline molecular sieves in order to improve their catalytic performances. U.S. Pat. No. 5,250,484 discloses a method for making a surface inactivated catalyst composition comprising acidic porous crystalline material, in particular ZSM-23, having active internal Broensted acid sites and containing surface inactivating material having boron to nitrogen bonds. The method involves contacting the surface of the molecular sieve with aqueous ammonia borane solution. The modified catalysts are described for use in olefin oligomerization processes.

U.S. Pat. No. 6,046,371 discloses silylated silicoaluminophosphate compositions prepared by contacting calcined SAPOs with a silylating agent, preferably tetraalkyl orthosilicates and poly(alkylaryl)siloxanes. The silylated silicoaluminophosphate compositions are described as giving increased light olefin yields and decreased coke production, when used as catalysts in the conversion of oxygenated hydrocarbons to olefins.

U.S. Pat. No. 6,472,569 discloses catalyst systems comprising a silicoaluminophosphate impregnated with a compound selected from the group consisting of phosphoric acid, boric acid, tributyltin acetate, and combinations of any two or more thereof. These catalyst systems are described as giving increased light olefin yields and decreased coke production, when used as catalysts in the conversion of oxygenated hydrocarbons and/or ethers.

PCT Application WO 02/085514-A2 discloses a process for modifying a microporous framework defined by nanocages, such as SAPO-18 or SAPO-34. The modified microporous framework comprises and an inorganic compound in at least one of the nanocages, wherein said inorganic compound is a product formed by a reaction of a second inorganic molecule that has a kinetic diameter smaller than the kinetic diameter of the inorganic compound. The second inorganic compound is selected from the group consisting of $PH_3$, $SiH_4$, $Si_2H_6$ and $B_2H_6$. The inorganic compound may be selected from the group consisting of phosphoric acid, boric acid, silica, a product of the hydrolysis of $PH_3$, a product of the hydrolysis of $SiH_4$, a product of the hydrolysis of $Si_2H_6$, a product of the hydrolysis of $B_2H_6$, a product of the oxidation of $PH_3$, a product of the oxidation of $SiH_4$, a product of the oxidation of $Si_2H_6$ and a product of the oxidation of $B_2H_6$. This document discloses more specifically a process for modifying H-SAPO-34 by treating H-SAPO-34 with $PH_3$ and methanol in a reactor at 250° C., followed by heating to 600° C. The method requires the presence of methanol to form $P(CH_3)_3$ and $P(CH_3)_4^+$ species in the SAPO-34 nanocages. According to this document, the modified H-SAPO-34 delivers higher ethylene selectivity than unmodified H-SAPO-34.

Despite the various molecular sieve modifications reported in the literature, there remains a need to find other methods for improving molecular sieve catalytic performances, in order to decrease the selectivity of these molecular sieves to undesired saturated hydrocarbons and to increase their selectivity to desired light olefins (ethylene and propylene), when used as catalysts in the conversion of oxygenated hydrocarbons.

SUMMARY OF THE INVENTION

The present invention provides a method for modifying a microporous metalloaluminophosphate molecular sieve, the method comprising the steps of a) introducing a compound containing at least one M-X group within the cages of said microporous molecular sieve; and b) reacting said compound containing at least one M-X group with the acid groups located in the cages of the molecular sieve, wherein the compound containing at least one M-X group is selected from the group consisting of compounds of formula $MX_3$, compounds of formula $M_2X_6$, and mixtures thereof, M being a metal belonging to Group 13 of the Periodic Table, and each X independently being a hydrogen or halogen atom. Preferably, X is a hydrogen atom.

In a embodiment, reacting the compound containing at least one M-X group with the molecular sieve acid groups takes place at a temperature of from room temperature to 500° C., preferably at a temperature of from room temperature to 150° C.

In a separate preferred embodiment introducing a compound containing at least one M-X group within the cages of said microporous molecular sieve takes place by contacting the molecular sieve with a compound containing at least one M-X group in the gas phase.

In yet another preferred embodiment, reacting the compound containing at least one M-X group with the molecular sieve acid groups takes place under conditions that avoid the presence of water and/or alcohols.

In an embodiment, the modification method further comprises the step of c) restoring at least a portion, preferably all, of the acid groups located in the cages of the molecular sieve by submitting the molecular sieve to a thermal treatment, preferably at a temperature of from about 100° C. to about 500° C., more preferably at a temperature of from about 30° C. to about 400° C. and even more preferably at a temperature of from 50° C. to 200° C. This thermal treatment can take place in the presence of water, an alcohol, such as methanol, ethanol or mixtures thereof, nitrous oxides, carbon monoxide, carbon dioxide, sources of ammonia, and mixtures thereof. Preferably, thermal treatment is carried out in the presence of water in the gas phase at a temperature of from 50° C. to 300° C.

The invention also provides a microcrystalline metalloaluminophosphate molecular sieve having acid sites within its intracrystalline cages bound with a metal compound, the metal compound being selected from the group consisting of $MX_x$, $M_2X_y$, and mixtures thereof, wherein M is a metal belonging to Group 13 of the Periodic Table; x ranges from 1 to 2 and y ranges from 1 to 5, each X independently being a hydrogen atom or a halogen atom. Preferably, X is hydrogen.

In yet another embodiment, the invention provides a method of making molecular sieve catalyst particles, the method comprising a) combining a microcrystalline metalloaluminophosphate molecular sieve having acid sites within its intracrystalline cages bound with a metal compound, the metal compound being selected from the group consisting of $MX_x$, $M_2X_y$, and mixtures thereof, wherein M is a metal belonging to Group 13 of the Periodic Table; x ranges from 1 to 2 and y ranges from 1 to 5, each X independently being a hydrogen atom or a halogen atom, with at least one binder and optionally at least one matrix to form a catalyst preparation mixture; b) forming catalyst particles from the catalyst preparation mixture obtained at step a); c) submitting the catalyst particles to a thermal treatment at a temperature of from about 30° C. to about 700° C.

The present invention also provides a microcrystalline metalloaluminophosphate molecular sieve having the AFX framewok type and comprising within its cages and/or channels a compound containing at least one M-O group, wherein M is a metal belonging to Group 13 of the Periodic Table and the compound containing at least on M-O group occupies up to 60% of the volume of the cages and channels of the molecular sieve.

In yet a separate embodiment, the invention provides a hydrocarbon conversion process comprising the steps of: (a) introducing a feedstock to a reactor system in the presence of a microcrystalline metalloaluminophosphate molecular sieve having the AFX framewok type and comprising within its cages and/or channels a compound containing at least one M-O group, wherein M is a metal belonging to Group 13 of the Periodic Table and the compound containing at least on M-O group occupies up to 60% of the volume of the cages and channels of the molecular sieve; (b) withdrawing from the reactor system an effluent stream; and (c) passing the effluent gas through a recovery system recovering at least the one or more conversion products.

The present invention also provides a process for making olefins from an oxygenate feedstock comprising the steps of a) providing a metalloaluminophosphate molecular sieve; b) introducing a compound containing at least one M-X group within the cages of said microporous molecular sieve; c) reacting said compound containing at least one M-X group with the acid groups located in the cages of the molecular sieve, wherein the compound containing at least one M-X group is selected from the group consisting of compounds of formula $MX_3$, compounds of formula $M_2X_6$, and mixtures thereof, M being a metal belonging to Group 13 of the Periodic Table, and each X independently being a hydrogen or halogen atom; d) restoring at least a portion of the acid groups located in the cages of the molecular sieve by submitting the molecular sieve to a thermal treatment; e) contacting the molecular sieve obtained at step d) with the oxygenate feedstock; f) recovering an olefin product.

In all these embodiments, the preferred metal M is either aluminum or boron, or a mixture thereof. The preferred metalloaluminophosphate molecular sieve is a small pore or medium pore metalloaluminophosphate molecular sieve, more preferably a silicoaluminophosphate molecular sieve and most preferably a silicoaluminophosphate molecular sieve having the CHA or AFX framework type.

When used to catalyze the formation of olefins from oxygenate feedstocks, such as feedstocks containing methanol and/or dimethyl ether, the modified molecular sieves of the present invention provide higher light olefin selectivities than the corresponding unmodified molecular seives.

BRIEF DESCRIPTION OF THE DRAWINGS

The present invention will be better understood by reference to the Detailed Description of the Invention when taken together with the attached drawings wherein.

DETAILED DESCRIPTION OF THE INVENTION

Introduction

Figure 1:
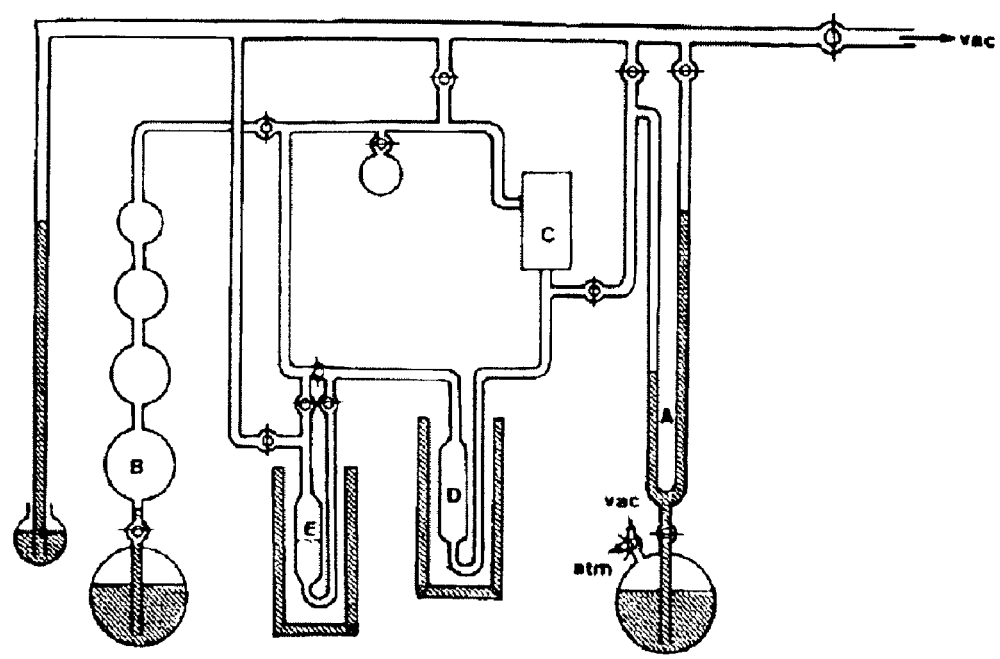
FIG. 1 shows a dynamic gas-volumetric adsorption apparatus suitable for treatment of metalloaluminophosphate molecular sieves with gases containing a compound containing at least one M-X group.

Molecular sieve materials such as metalloaluminophosphate molecular sieves (MeAPOs) comprise a three-dimensional microporous crystal framework structure. After calcination, they possess a void volume consisting of channels and cages within their molecular framework. Recent studies by Kolboe et al. and by Haw et al. indicate that the catalytic conversion of methanol to olefins over SAPO-34 proceeds through a so-called "hydrocarbon pool" mechanism (Dahl, I. M., Kolboe, S., *Catal. Lett.*, 1993, 20, 329–336; Dahl, I. M., Kolboe, S., *J. Catal.*, 1994, 149, 458–464; Dahl, I. M., Kolboe, S., *J. Catal.*, 996, 161, 304–309; Goguen, P. W., Xu, T., Barich, D. H., Skloss, T. W., Song, W., Wang, Z., Nicholas, J. B., Haw, J. F., *J. Am. Chem. Soc.*, 1998, 120, 2650–2651; Song, W., Haw, J. F., Nicholas, J. B., Heneghan, C. S., *J. Am. Chem. Soc.*, 2000, 122, 10726–10727; Song, W., Haw, J. F., *J. Am. Chem. Soc.*, 2001, 123, 4749–4754; Song, W., Fu, H., Haw, J. F., *J. Phys. Chem. B*, 2001, 105, 12839–12843; Arstad, B., Kolboe, S., *Catal. Lett.*, 2001, 71, 209–212; Arstad, B., Kolboe, S., *J. Am. Chem. Soc.*, 2001, 123, 8137–8138; WO 02/085514). According to this mechanism, and without wishing to be bound to any theory, methylated aromatic compounds (methylated benzene and/or methylated naphthalene) form within the molecular sieve cages during the methanol to olefins conversion. The amount and type of methylated aromatic compounds present in the molecular sieve cages are dependent on the number of acid sites in the molecular sieve cages, as well as on the size and shape of the molecular sieve cages. The amount and type of aromatic compounds present in the cages is believed to influence product selectivity during the conversion of methanol to light olefins.

The present invention is directed toward a method of partially filling the void volume of a microporous molecular sieve with a Volume Modifier, while maintaining the acid sites within the channels and cages of the molecular sieve. After this modification, the molecular sieve possesses increased selectivity to desired products, such as ethylene and propylene, and lowered selectivity to undesired products, such as propane and saturated and unsaturated hydrocarbons having more than 3 carbon atoms, when used to catalyze the conversion of oxygenates. The present invention provides an important catalytic improvement, not only for molecular sieves already known for their good performances in the oxygenates-to-olefins conversion such as SAPO-34, but also for other molecular sieves.

The modified molecular sieves of the present invention are obtained by modifying crystalline molecular sieves that can have a wide range of chemical and physical characteristics. Molecular sieves have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type molecular sieves for which a structure has been established, are assigned a three letter code and are described in the *Atlas of Zeolite Framework Types,* 5th edition, Elsevier, London, England (2001), which is herein fully incorporated by reference.

Crystalline molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1–67, Elsevier Science, B. V., Amsterdam, Netherlands (2001). In a preferred embodiment, the molecular sieve is a metalloaluminophosphate molecular sieve, more preferably a silicoaluminophosphate molecular sieve, having 8- or 10-ring structures, most preferably having 8-rings and an average channel pore size less than about 5 Å, preferably in the range of from 3 Å to about 5 Å, more preferably from 3 Å to about 4.5 Å, and most preferably from 3.5 Å to about 4.2 Å.

Non-limiting examples of small pore molecular sieves are molecular sieves that have the framework types AEI, AFT, AFX, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO. Non-limiting examples of medium pore molecular sieves are molecular sieves that have the framework types AFO, AEL, EUO, HEU, FER, MEL, MFI, MTW, MTT, TON. Non-limiting examples of large pore molecular sieves are molecular sieves that have the framework types BEA, CFI, EMT, FAU, LTL, MWW. Other non-limiting examples of molecular sieves include ANA, clO, DON, GIS, MER, MOR, and SOD. Non-limiting examples of the preferred molecular sieves, particularly for converting an oxygenate containing feedstock into olefin(s), include AEL, AFX, BEA, CHA and KFI. In a more preferred embodiment, the molecular sieve of the invention has a CHA, KFI or AFX topology, or a combination thereof, most preferably an AFX topology.

Non limiting examples of preferred molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. The more preferred molecular sieves of the invention include one or a combination of SAPO-17, SAPO-34, SAPO-35, SAPO-44, SAPO-56, AlPO-18 and AlPO-34, even more preferably SAPO-56.

Crystalline Molecular Sieve Synthesis

The crystalline molecular sieves that can be modified according to the present invention may be prepared by a wide range of methods, well known in the art. Generally, molecular sieves are synthesized by the hydrothermal crystallization of one or several of a source of aluminum, a source of phosphorous, a templating agent, and a source of metal, preferably silicon. Typically, a combination of the selected sources of aluminum and phosphorous, optionally with one or more templating agents and/or one or more sources of silicon and/or other metal, are placed in a sealed pressure vessel, optionally lined with an inert plastic such as polytetrafluoroethylene, and heated, at a crystallization pressure and crystallization temperature, until a crystalline material is formed, and then recovered by filtration, centrifugation and/or decanting. In a preferred embodiment, at least one templating agent and at least one source of metal, most preferably silicon, is used.

Non-limiting examples of silicon sources include silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudoboehmite, gibbsite and aluminum trichloride, or any combinations thereof. A preferred source of aluminum is pseudoboehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $AlPO_4$, phosphorous salts, or combinations thereof. The preferred source of phosphorous is phosphoric acid, particularly when producing a silicoaluminophosphate.

Templating agents are generally compounds that contain elements of Group 15 of the Periodic Table of Elements, particularly nitrogen, phosphorus, arsenic and antimony, more preferably nitrogen or phosphorous, and most preferably nitrogen. Typical templating agents of Group 15 of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-substituted amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium compounds including salts thereof, and tetrabutylammonium compounds including salts thereof, cyclohexylamine, morpholine, di-n-propylamine (DPA), tripropylamine, triethylamine (TEA), triethanolamine, piperidine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methylpyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

Depending on the ratio and the type of ingredients used to prepare the molecular sieve, molecular sieves with high or low silicon (Si) to aluminum (Al) ratios can be obtained. The pH of a reaction mixture containing at a minimum a silicon-, aluminum-, and/or phosphorous-composition, and a templating agent, should be in the range of from 2 to 10.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Treatment with M-X Group Containing Compounds

According to the present invention, the cage volume of a microporous molecular sieve is modified by introducing a compound containing at least one M-X group within the cages and/or channels of the microporous molecular sieve, wherein M is selected from the group consisting of metals belonging to Group 13 of the Periodic Table [using the IUPAC numbering system described in the *CRC Handbook of Chemistry and Physics*, 78th Edition, CRC Press, Boca Raton, Fla. (1997)], and X is a hydrogen or halogen atom. Preferably, the compound containing at least one M-X group is selected the group consisting of compounds of formula $MX_3$, compounds of formula $M_2X_6$, and mixtures thereof, M being a metal belonging to Group 13 of the Periodic Table, and each X independently being a hydrogen or halogen atom.

This treatment can be applied to various types of molecular sieves, including small pore, medium pore and large pore molecular sieves. An important feature of the present invention is that the compound containing at least one M-X group (hereinafter referred to as Treating Agent) must be able to penetrate within the void volume of the molecular sieve. Before using the Treating Agent, it is thus preferred to submit the molecular sieve to a heat treatment or calcination in order to remove the compounds that may be present in the void volume of the molecular sieve. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

Also, it is preferable to use a Treating Agent having a kinetic diameter no larger (equal to or smaller), preferably smaller than the pore opening size of the molecular sieve. In a preferred embodiment, the Treating Agent is incorporated within the cage volume of a metalloaluminophosphate molecular sieve, most preferably a small pore metalloaluminophosphate molecular sieve.

The Treating Agent is more preferably selected from the group consisting of $AlH_3$, $AlCl_3$, $BH_3$, $BF_3$, $B_2H_6$ and mixtures thereof, even more preferably from the group consisting of $BH_3$, $B_2H_6$ and mixtures thereof. In the embodiment where X is a halogen atom, it is preferably either fluorine or chlorine. Most preferably, X is a hydrogen atom. In the most preferred embodiment, the compound containing at least one M-X group is $B_2H_6$.

The Treating Agent can be introduced within the void volume of the molecular sieve by various methods that involve contacting the molecular sieve with the Treating Agent. One method consists in placing the molecular sieve in a gas atmosphere containing the Treating Agent, optionally in the presence of a diluting inert gas. In a preferred method, the molecular sieve is placed in a closed vessel containing the Treating Agent in the gas phase. Another method consists in contacting a liquid Treating Agent or a solution or slurry of the Treating Agent with the microporous molecular sieve under conditions allowing the Treating Agent to reach the cages within the framework of the molecular sieve. Non-limiting examples of such conditions include incipient wetness, immersion in the liquid with or without stirring. In the embodiment where the Treating Agent is dissolved in a solvent, the solvent is preferably an organic aprotic solvent such as, for example, acetonitrile, dimethyl ether, diethyl ether, tetrahydrofuran, dimethyl formamide, liquid hydrocarbons such as benzene, toluene, alkanes having from 5 to 20 carbon atoms, cycloalkanes having from 5 to 20 carbon atoms, and mixtures thereof.

The treatment may be carried out within a wide range of temperatures, including temperatures below room temperature, room temperature and temperatures above room temperature, depending on the physical and chemical properties of the molecular sieve and Treating Agent used.

A convenient range of temperature is from room temperature up to 500° C., provided the Treating Agent is stable at the chosen temperature. In the embodiment where the Treating Agent is $BX_3$ or $AlX_3$, where X is a halogen atom, temperatures up to 500° C. are usually suitable. However, where the Treating Agent is, for example, $B_2H_6$, treatment is preferably carried out at a temperature below 250° C. to avoid chemical alteration of the Treating Agent. For temperature sensitive Treating Agents, typical preferred temperatures range from room temperature to 150° C., more preferably from room temperature to 100° C.

In a preferred embodiment, contacting the molecular sieve with the Treating Agent takes place under conditions that avoid the presence of protic substances, such as for example, water and/or alcohols. For this purpose, the equipment, molecular sieves and solvents are carefully cleaned, dried and purified before contacting the molecular sieve with the Treating Agent.

Without being bound to any particular theory, the M-X Treating Agent is believed to react within the void volume of the molecular sieve with the molecular sieve OH groups located in the cages of the molecular sieve. The reaction is accompanied by release of H—X and results in binding of M groups to the molecular sieve framework, resulting in a first treated molecular sieve. The first treated molecular sieve thus has acid sites within its intracrystalline cages bound with a metal compound, the metal compound being selected from the group consisting of $MX_x$, $M_2X_y$, and mixtures thereof, wherein M is a metal belonging to Group 13 of the Periodic Table; x ranges from 1 to 2 and y ranges from 1 to 5, each X independently being a hydrogen atom or a halogen atom. Preferably, M is boron or aluminum and X is hydrogen.

The first treated molecular sieve is then typically submitted to a thermal treatment, in order to remove residual treating material, and to restore at least a portion, preferably all, of the molecular sieve OH groups present in the channels and cages of the molecular sieve. Optionally, this thermal treatment is performed in the presence of a chemical agent which helps restore the molecular sieve OH groups. Non-limiting examples of such agents include water, alcohols, such as methanol or ethanol, nitrous oxides, carbon monoxide, carbon dioxide, sources of ammonia, and mixtures thereof. In a preferred embodiment, the agent that helps restore the molecular sieve OH groups is water or methanol, more preferably, water, most preferably water in the vapor phase. Thermal treatment of the first treated molecular sieve is typically carried out at a temperature of from about 100° C. to about 700° C., preferably from 30° C. to 400° C., most preferably 50° C. to 200° C. Typical durations range from 10 minutes to 48 hours, preferably from 20 minutes to 24 hours, more preferably from 30 minutes to 16 hours.

In the embodiment in which thermal treatment is carried out in the presence of agent that helps restore the molecular sieve OH groups, the agent is preferably in the gas phase and thermal treatment is carried out at a temperature of from room temperature to 500° C., preferably of from 25° C. to 300° C., more preferably of from 50° C. to 200° C.

Thermal treatment may optionally be followed by a calcination step. Typical calcination temperatures are in the range from about 400° C. to about 1,000° C., preferably from about 500° C. to about 800° C., and most preferably from about 550° C. to about 700° C., preferably in a calcination environment such as air, steam, nitrogen, helium, flue gas (combustion product lean in oxygen), or any combination thereof. In an embodiment, thermal treatment and calcination can be carried out simultaneously, optionally in the presence of the agent that helps restore the molecular sieve OH groups.

After thermal treatment, optionally accompanied or followed by calcination, a second treated molecular sieve is obtained. This second treated molecular sieve has a compound containing at least one M-O group, preferably containing only M-O groups, and hereinafter referred to as "Volume Modifier", within its cages. Preferably, the Volume Modifier is present in an amount sufficient to fill as much as possible of the void volume (channels and cages, preferably the cages) of the molecular sieve, without affecting the catalytic activity of the molecular sieve. The preferred weight and volume of Volume Modifier will vary within a wide range of possible limits, depending on the molecular sieve used, in particular its channel and cage volume size, the size and chemical nature of the Treating Agent and the desired catalytic performances. Preferably, the Volume Modifier occupies at least 60% of the cage volume, more preferably at least 50% of the cage volume.

In order to achieve the desired level of void volume reduction, the treatment sequence described above can be repeated as many times as necessary. Each treatment sequence will result in the formation of additional Volume Modifier within the void volume of the molecular sieve Typically, molecular sieves used in catalytic processes, especially on a commercial scale, are formulated into catalyst compositions. Formulation can occur at several stages of the molecular sieve treatment according to the present invention: before treatment, after formation of the first treated molecular sieve but before formation of the second treated molecular sieve (i.e. before the thermal treatment step) or after formation of the second treated molecular sieve (i.e. after the thermal treatment step). Catalyst formulation can thus be done either on the crystalline molecular sieve, on the first treated molecular sieve or on the second treated molecular sieve, herein collectively referred to as molecular sieve composition.

In all three embodiments, a catalyst composition is made or formulated by combining a molecular sieve composition, with a binder and/or a matrix material. These formulated catalyst compositions are then formed into useful shape and sized particles by well-known techniques such as spray drying, pelletizing, extrusion, and the like.

There are many different binders that are useful in forming catalyst compositions according to the invention. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

In a preferred embodiment, the molecular sieve composition is combined with one or more matrix material(s). Matrix materials are typically effective in reducing overall catalyst cost, act as thermal sinks assisting in shielding heat from the catalyst composition for example during regeneration, densifying the catalyst composition, and increasing catalyst strength such as crush strength and attrition resistance.

Non-limiting examples of matrix materials include one or more of: clays, rare earth metal oxides, non-active metal oxides including magnesia, thoria, beryllia, quartz, silica or sols, and mixtures thereof, for example silica-magnesia, silica-zirconia, silica-titania, silica-alumina and silica-alumina-thoria. Preferably, the matrix material is a clay.

Upon combining the molecular sieve composition and the matrix material, and/or binder, in a liquid to form a slurry, mixing, preferably rigorous mixing is needed to produce a substantially homogeneous mixture containing the molecular sieve composition. Non-limiting examples of suitable liquids include one or a combination of water, alcohol, ketones, aldehydes, and/or esters. The most preferred liquid is water.

In one embodiment, the slurry of the molecular sieve composition, binder and matrix material is mixed or milled to achieve a sufficiently uniform slurry of sub-particles of the molecular sieve catalyst composition that is then fed to a forming unit that produces the molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve composition and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 $\mu$m to about 300 $\mu$m, preferably from about 50 $\mu$m to about 250 $\mu$m, more preferably from about 50 $\mu$m to about 200 $\mu$m, and most preferably from about 65 $\mu$m to about 90 $\mu$m.

Once the catalyst composition is formed in a substantially dry or dried state, to further harden and/or activate the formed catalyst composition, a heat treatment such as calcination, at an elevated temperature is usually performed. In the embodiment where formulation of the first treated molecular sieve is performed, this calcination treatment can replace or be part of the thermal treatment used to generate the compound having at least one M-O bond in the cages and/or channels of the molecular sieve. A conventional calcination environment to harden the catalyst particles is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In a preferred embodiment, the catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Catalytic Processes

The molecular sieve compositions and catalyst compositions described above are useful in a variety of processes including: cracking, of for example a naphtha feed to light olefin(s) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product;

reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

The preferred process of the invention is a process directed to the conversion of a feedstock comprising one or more oxygenates to one or more olefin(s). In a preferred embodiment of the process of the invention, the feedstock contains one or more oxygenates, more specifically, one or more organic compound(s) containing at least one oxygen atom. In a more preferred embodiment, the feedstock contains methanol and/or dimethyl ether, and most preferably methanol.

The feedstock containing one or more oxygenates, is converted in the presence of a molecular sieve catalyst composition into olefin(s) having 2 to 6 carbons atoms, most preferably ethylene and/or propylene.

In one embodiment, the feedstock can contain one or more diluent(s), typically used to reduce the concentration of the feedstock, and generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. The diluent is used either in a liquid or a vapor form, or a combination thereof. The diluent is either added directly to a feedstock entering into a reactor or added directly into a reactor, or added with a molecular sieve catalyst composition.

The process for converting one or more oxygenates to olefins, in the presence of a molecular sieve catalyst composition of the invention, is carried out in a reactor system, operated as a fixed bed process, a fluidized bed process (including a turbulent bed process), preferably a continuous fluidized bed process, and most preferably a continuous high velocity fluidized bed process. The processes of the invention can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor. Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol and dimethyl ether is in the range of from about 20 hr$^{-1}$ to about 300 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

The coked (used) molecular sieve catalyst composition is withdrawn from the disengaging vessel and introduced to the regeneration system. The regeneration system comprises a regenerator where the coked catalyst composition is contacted with a regeneration medium, preferably a gas containing oxygen, under general regeneration conditions of temperature, pressure and residence time. The regeneration temperature is in the range of from about 200° C. to about 1500° C., preferably from about 300° C. to about 1000° C., more preferably from about 450° C. to about 750° C., and most preferably from about 550° C. to about 700° C. The regeneration pressure is in the range of from about 15 psia (103 kpaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

In an embodiment, a portion of the molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a de-methanizer, preferably a high temperature de-methanizer, a de-ethanizer, a de-propanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a methanol-to-olefins process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in Kirk-*Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process are described in EP-B-0 933 345, which is herein fully incorporated by reference.

In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

EXAMPLES

In order to provide a better understanding of the present invention including representative advantages thereof, the following examples are offered.

Methods

Infrared Spectroscopy

DRIFTS (Diffuse Reflectance Infrared Fourier Transform Spectroscopy) spectra were recorded on a Nicolet Nexus FTIR spectrometer equipped with an in situ DRIFTS cell (SpectraTech) and an MCT detector. The samples were mixed with KBr (95% KBr; 5% sample). The measurements were performed in vacuum at 400° C. after degassing the samples in situ for 15 minutes. Pure KBr was run as a reference. Spectra were obtained by co-adding 500 scans. The spectral resolution was 4 $cm^{-1}$.

Transmission spectra were measured on a Nicolet 20SX spectrometer equipped with a vacuum cell and a DTGS detector. Self-supporting discs with a thickness of 20 $mg/cm^2$ were used. The spectra were recorded at room temperature. 100 scans were co-added with a spectral resolution of 4 $cm^{-1}$.

MAS NMR Spectroscopy $^1H$, $^{11}B$, $^{27}Al$ and $^{29}Si$ MAS NMR measurements were done at room temperature on Bruker AMX360 and Chemagnetics CMX-II wide bore spectrometers operating at a static magnetic field of 8.4 T and 11.7 T, respectively. The $^{11}B$ and $^{27}Al$ MAS NMR spectra were recorded using single pulse Bloch decay and H decoupling techniques on samples spinning at the magic angle at rates of about 10–13 kHz. The $^{29}Si$ spectra were recorded using single pulse Bloch decay and cross polarization techniques on samples spinning at the magic angle at rates of about 5 kHz. The $^1H$ MAS NMR spectra were recorded using single pulse Bloch decay techniques on dehydrated samples spinning at the magic angle at rates of about 10 kHz. Chemical shifts for $^1H$, $^{11}B$, $^{27}Al$, and $^{29}Si$ were calibrated using tetramethylsilane, $BF_3(OEt_2)$, 0.1M $Al(H_2O)_6^{3+}$, and tetramethylsilane, respectively.

XRD

X-ray Diffractograms were recorded on a Philips PW 1840 powder diffractometer, using Ni-filtered Cu Kα radiation (X=0.154 nm).

Methanol Adsorption Capacity

The methanol adsorption capacity is measured in a gravimetric adsorption apparatus, which comprised a quartz spring. After degassing the SAPO samples in vacuum at 200° C., the sample was cooled to room temperature and methanol vapour was allowed into the system at room temperature. By measuring the weight changes at regular time intervals, not only the adsorption capacity but also the adsorption kinetics was measured. The methanol adsorption capacity (MAC) is the amount of methanol adsorbed when the system is in equilibrium and is given as the increase in weight (in %) of a dehydrated SAPO after methanol uptake.

Methanol Conversion During MTO

The MTO reaction (Methanol-to-Olefins) was performed in a stainless steel, fixed bed continuous reactor. A mixture of water and methanol (50:50 by weight) was added as feed. The reaction was carried out at 450° C., a reactor pressure of 15 psig and a WHSV of 13 g/g.hr. Reaction products were analyzed with an on-line GC. Methanol conversion is calculated as 100 −(wt. % methanol+wt. % DME) left in the product.

The results of MTO performance tests are expressed using the following definitions $B_2H_6$ content, means the cumulative amount (in mmoles) of Treating Agent loaded in the molecular sieve after all treatment sequences;

$CH_4$, means methane selectivity;

$C_2^=$, means ethylene selectivity;

$C_2^0$, means ethane selectivity;

$C_3^=$, means propylene selectivity;

$C_3^0$, means propane selectivity;

Total $C_4^+$, means selectivity to all hydrocarbon having more than 3 carbon atoms; all selectivities being expressed as weight percent average selectivities.

Lifetime, means total amount (gram) of (MeOH+DME) converted per gram of calcined molecular sieve.

Example 1

Microcrystalline Molecular Sieves 1.1. SAPO-11 (AEL FRAMEWORK TYPE)

SAPO-11 was prepared according to the following procedure. Water, pseudoboehmite alumina (Condea Pural SB), hexadecylamine dissolved in ethanol, then dipropylamine followed by tetraethylorthosilicate and 85 wt % $H_3PO4$ (Aldrich) were mixed in sequence with a high shear mixer (Euro-Turrax T20 basic with dispersing element S 20–25 NK-19 G), in order to form a uniform gel. The molar ratio of the ingredients was as follows:

0.4 $SiO_2$:$Al_2O_3$:$P_2O_5$:0.16 hexadecylamine:7.5 EtOH:2DPA:40$H_2O$

The thick gel was placed in a stainless steel autoclave, heated in 2 hrs to 195° C. and kept there for 24 hrs without stirring. The solid product was centrifuged and washed once with deionized water, then two times with a mixture of water and ethanol and then three times with deionized water and was then dried at 120° C. in an oven overnight. The solid product yield was 14.6%. XRD pattern shows that the product is SAPO-11.

1.2. SAPO-17 (ERI FRAMEWORK TYPE)

SAPO-17 was prepared according to the procedure described at example 26 of U.S. Pat. No. 4,440,871.

SAPO-17 was prepared using cyclohexylamine as the templating agent. The reaction mixture was prepared by combining 4.08 grams of aluminum isopropoxide [Al (OC3H7)3] with a solution of 2.31 grams of 85 wt. % orthophosphoric acid (H3PO4) in 7.98 grams of H2O, stirring until homogeneous, and then adding 0.20 grams of an aqueous silica sol containing 30 wt.-% SiO2. The resulting mixture was stirred until it was homogeneous. To this mixture was added 0.50 grams of cyclohexylamine (CHA), and the mixture stirred until homogeneous. The composition of the final reaction mixture in molar oxide ratios was:

1.0CHA:0.1$SiO_2$:$Al_2O_3$:$P_2O_5$:50$H_2O$

The reaction mixture was sealed in a 15 cc stainless steel pressure vessel lined with polytetrafluoroethylene and heated in an oven at 200° C. at autogenous pressure for 50 hours. The solid reaction product was recovered by filtration, washed with water, and dried in air at 100° C. The composition of the product corresponds to the formula in terms of molar oxide ratios: $Al_2O_3$:0.901 $P_2O_5$:0.072 $SiO_2$. XRD pattern shows that the product is SAPO-17.

1.3. SAPO-18 (AEI FRAMEWORK TYPE)

SAPO-18 was prepared according to the following procedure. Phosphoric acid (85 wt % $H_3PO_4$, Aldrich), water, pseudoboehmite alumina (Condea Pural SB), Cabosil L-90 silica dissolved in N,N-diisopropylethylamine (Fluka) were mixed, in sequence, in order to form a uniform gel. The molar ratio of the ingredients was as follows:

0.057$SiO_2$:$Al_2O_3$:0.9$P_2O_5$:2.2DIPEA:50.2$H_2O$

The synthesis mixture was placed in a 2L autoclave, stirred and heated in 8 hrs to 160° C. and kept for 48 hrs at 160° C. The solid product was centrifuged and washed several times with deionized water and was then dried in a 120° C. oven overnight. The solid product yield was 12%. XRD pattern shows that the product is SAPO-18.

1.3. SAPO-34 (CHA FRAMEWORK TYPE)

SAPO-34 was prepared according to procedure described below. The following ingredients were mixed with a Hobart mixer, in sequence, into a uniform gel: pseudoboehmite alumina (Condea Pural SB) and $H_2O$, 85 wt % $H_3PO_4$ (Aldrich), Ludox AS-40, tetraethylammoniumhydroxide (35%, Sachem) and dipropylamine. At the end 400 wt ppm seeds are added. The molar ratio of the ingredients is as follows:

0.3SiO$_2$:Al$_2$O$_3$:P$_2$O$_5$:TEAOH:1.62DPA:53H$_2$O

The synthesis mixture was placed in a 2L stainless steel autoclave without stirring. The following crystallization program was used: heat in 1 h to 90° C., keep at 90° C. for 24 hrs, then heat in 2 hrs to 175° C. and keep at 175° C. for 60 hrs. The solid product was centrifuged and washed several times with deionized water and was then dried in a 120° C. oven overnight. The solid product yield was 12%. XRD pattern shows that the product is SAPO-34.

1.4. SAPO-56 (AFX FRAMEWORK TYPE)

SAPO-56 was prepared based on the procedure described in S. T. Wilson, et al., Microporous and Mesoporous Materials, 28, 1999, p. 125–137. SAPO-56 was synthesized from the gel composition:

1.5TMHD:0.45SiO$_2$:1.0Al$_2$O$_3$:1.0P$_2$O$_5$:40H$_2$O where TMHD is N,N,N',N'-tetramethyl-hexane-1,6-diamine (Aldrich). The oxide raw materials were Cab-o-sil® (fumed silica), Catapal A® (pseudo-boehmite alumina) and 85% orthophosphoric acid. The reactants were combined with vigorous mixing in the order: water, acid, alumina, silica, amine. The reaction mixture was crystallized quiescently at 200° C. for 96 h. The product was recovered by filtration. X-ray analysis showed that the product was pure SAPO-56. Elemental analysis of a typical SAPO-56 preparation gave the following composition (in molar ratio of oxides): Al$_2$O$_3$:0.731 P$_2$O$_5$:0.676 SiO$_2$. XRD pattern shows that the product is SAPO-56.

EXAMPLE 2

Treatment of SAPO-34 with $B_2H_6$

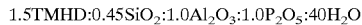

2.1. Molecular Sieve Treatment

Diborane ($B_2H_6$) was obtained as a gas (10% in hydrogen, electronic grade) packaged in electropolished stainless steel lecture bottle) from Aldrich Chemical company, Inc (Sigma-Aldrich NV/SA K. Cardijnplein 8, B-2880 Bornem). Before use $B_2H_6$ was cryogenically seperated from hydrogen.

As-synthesized SAPO-34 was activated (calcined) prior to the modification. Calcination was performed in a muffle furnace at 625° C. for 4 hours under ambient air (heating rate: 5° C./min). The calcined SAPO-34 was transferred into a dynamic gas-volumetric adsorption apparatus as illustrated in FIG. 1. The apparatus consists of two calibrated volumes, the 'dead volume' and the 'sample container'. The dead volume consists of a Hg-manometer (A), a fixed-step gas burette (B), a circulation pump (C) and a cold trap (D). The dead volume is separated from the sample container (E) by two valves and by shutting the interconnecting valve it is possible to enforce a unidirectional flow through the sample container. Both volumes are connected to a high vacuum system (rotation pump+diffusion pump), which allows a pressure reduction to <<0.1 Pa. The apparatus is constructed to maintain this vacuum for several days. The calcined molecular sieve sample was degassed in sample container (E) overnight in vacuum at 300° C. and diborane in the gas phase was contacted in situ with the molecular sieve for 30 to 60 minutes at 50° C. After completion of the reaction and evacuation under vacuum of excess $B_2H_6$ and of the hydrogen formed during the reaction, the sample was heated to 150° C. under vacuum. A flask containing water was then connected to the apparatus and water vapour was allowed into the system while the molecular sieve sample was maintained at 150° C., in order to hydrolyze the hydride groups. The boron-treated samples were then heated overnight to 400° C. under vacuum. The sample was then allowed to cool down to room temperature under vacuum. The diborane treatment sequence described above was repeated until the desired boron loading was achieved. Boron loading corresponds to the cumulative volume of $B_2H_6$ consumed during all the successive treatments. Once the desired boron loadings were achieved, the samples were stored under inert atmosphere.

2.2. Infrared Spectroscopy

Figure 2:
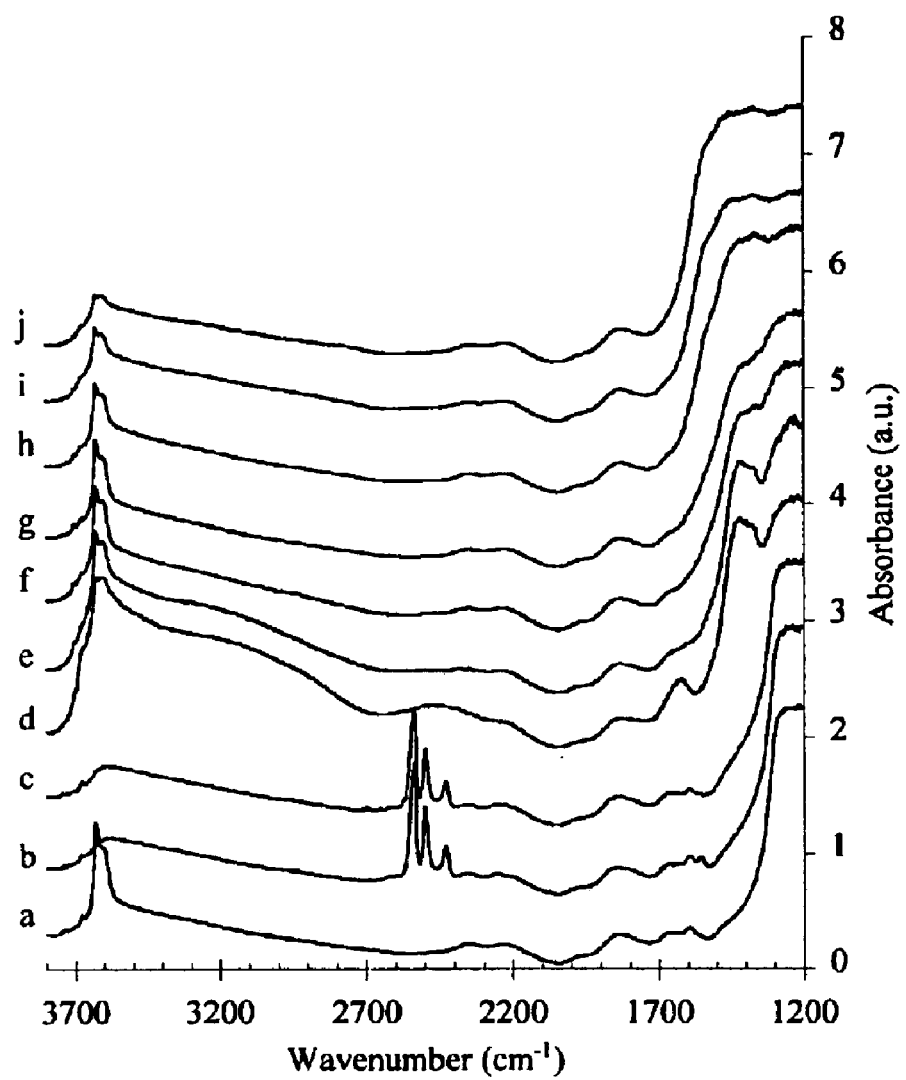
FIG. 2 shows vacuum Transmission IR spectra obtained during the diborane treatment of SAPO-34 for (a) parent SAPO-34, (b) after reaction with $B_2H_6$ at 50° C., (c) after heating to 150° C., (d) after hydrolysis reactions at 150° C., (e–g) after heating to 200° C., 300° C. and 400° C. respectively, (h–j) SAPO-34 after 3, 5 and 10 complete diborane treatments, respectively.

The boronation reaction was monitored by IR spectroscopy. FIG. 2 shows vacuum Transmission IR spectra obtained during the diborane treatment of SAPO-34 for (a) parent SAPO-34, (b) after reaction with $B_2H_6$ at 50° C., (c) after heating to 150° C., (d) after hydrolysis, (e-g) after heating to 200° C., 300° C. and 400° C. respectively, (h-j) SAPO-34 after 3, 5 and 10 complete treatment sequences, respectively.

Below 1300–1200 cm$^{-1}$ transmission was too low, resulting in saturated absorbance spectra. As shown by comparing spectra (a) and (b) of FIG. 2, the Brønsted sites at 3600–3625 cm$^{-1}$ are consumed during the first diborane treatment. This is accompanied by the appearance of new bands in the region 2400–2600 cm$^{-1}$, which are attributed to BH$_2$ chemisorbed on the acid sites. The diborane treated sample was then heated ex situ to 150° C. under vacuum to study secondary reactions. No significant changes are observed in the IR spectrum (spectrum (c)). After hydrolysis at 150° C. (curve (d)), the new bands in the region 2400–2600 cm-1 disappear and the Brønsted acid site bands at 3600–3625 cm$^{-1}$ reappear. A broad shoulder in the region from 2700 to 3500 cm$^{-1}$ is observed, which disappears after heating to 400° C. (spectra (d), (e) and (f)). The diborane treatment/hydrolysis/heat treament sequence was repeated ten times. Spectra (h), (i) and (j) show the IR spectra after 3, 5 and 10 treatment sequences, respectively. After each treatment sequences, the intensity of the B—O band increases. After 4 to 5 treatment sequences, the intensity of the Brønsted acid site bands decreases. Without wishing to be bound by any theory, the decrease in intensity of Brønsted acid site bands suggests that, after a certain boron loading, boron starts to interact with the cage acid sites of the molecular sieve. Before that stage, the data suggests that boron oxide, not bound to cage acid sites is formed in the cage volume of the molecular sieves. After 4–5 treatment sequences, SAPO-34 the void volume of SAPO-34 has been reduced by about 25–30 percent.

2.3. MAS NMR

The $^{27}$Al and the $^{31}$P MAS NMR spectra of the boron-treated SAPO-34 samples showed no changes in the chemical environment of both the Al and the P atoms. $^{11}$B NMR showed a broad peak at around 10 ppm, indicating the presence of $B_2O_3$. All measurements indicate that the interaction of the boron oxygen compounds with the molecular sieve framework is minor.

2.4. Void Volume

Methanol adsorption capacity (MAC) measurements confirmed that the void volume of SAPO-34 can be reduced to about 25% without significantly affecting the catalytic activity of the molecular sieve.

2.5. XRD Patterns

The XRD pattern of the samples after loading with the Volume Modifier were typical of SAPO-34, indicating no change to the framework structure of the molecular sieve.

EXAMPLE 3

Treatment of SAPO-56 with $B_2H_6$ 3.1. Molecular Sieve Treatment

Several SAPO-56 samples were treated with diborane ($B_2H_6$) according to the method described at example 2.1. The samples were loaded with amounts of diborane ranging from 0.68 to 3.67 mmoles of diborane per gram of SAPO-56.

3.2. Infrared Spectroscopy

Figure 3:
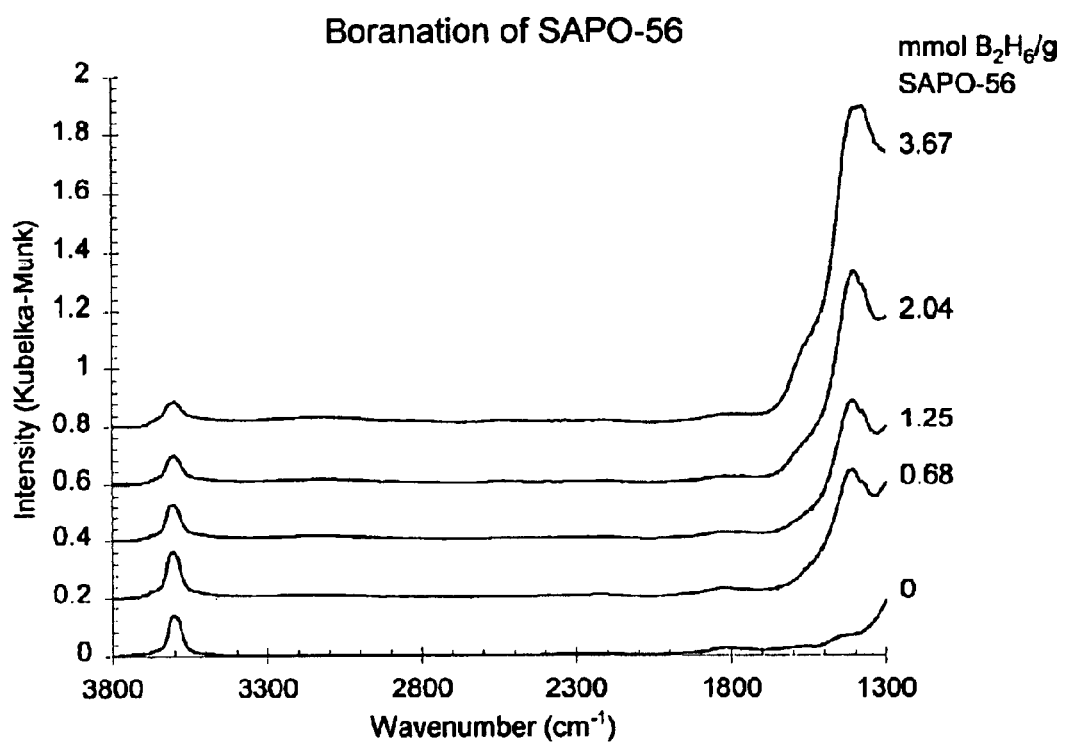
FIG. 3 shows in situ DRIFTS spectra obtained for SAPO-56 samples loaded with amounts of diborane ranging from 0.68 to 3.67 mmoles of diborane per gram of SAPO-56.

FIG. 3 shows the IR spectra obtained for these samples. As can be seen from FIG. 3, all treated SAPO-56 samples show an important residual acidity. The data indicate that boron oxygen compounds are formed in the SAPO-56 void volume. At low boron loadings, these boron oxygen compounds are formed without interacting with the molecular sieve acid sites. The void volume of SAPO-56 can be modified by boron oxide by up to about 50% without significantly affecting the catalytic activity of the molecular sieve.

3.3. Void Volume

Methanol adsorption capacity (MAC) measurements confirmed that the void volume of SAPO-56 can be reduced to about 50% without significantly affecting the catalytic activity of the molecular sieve.

3.4. XRD Patterns

The XRD pattern of the samples after loading with the Volume Modifier were typical of SAPO-56, indicating no change to the framework structure of the molecular sieve.

EXAMPLE 4

Treatment of SAPO-11 and SAPO-17 with $B_2H_6$ 4.1. Molecular Sieve Treatment

Several SAPO-11 and SAPO-17 samples were treated with diborane ($B_2H_6$) according to the method described at example 2.1. The samples were loaded with amounts of diborane ranging from 0.29 to 1.28 mmoles of diborane per gram of SAPO-11 and from 0.36 to 0.99 mmoles of diborane per gram of SAPO-17.

4.2. Infrared Spectroscopy

Infrared spectroscopy patterns followed the same trends as observed for SAPO-34 and SAPO-54.

4.3. Void Volume

Methanol adsorption capacity (MAC) measurements confirmed that the void volume of SAPO-11 and SAPO-17 can be reduced without significantly affecting the catalytic activity of the molecular sieve.

EXAMPLE 5

Catalytic Performance 5.1. SAPO-56

Several SAPO-56 samples were treated with diborane ($B_2H_6$) according to the method of example 3.1. (diborane loadings of 0.68, 1.25, 2.04 and 3.67 mmoles of diborane per gram of SAPO-56, respectively) and were tested for their catalytic performances in the conversion of methanol to olefins, using the general testing apparatus and procedure. The conditions during the methanol to olefins conversion were: reaction temperature: 450° C., pressure of 15 psig, WHSV of about 12 g/g.hr (mixture of $MeOH/H_2O$: 50/50 wt %; flow rate: 10 ml/h).

Figure 4A:
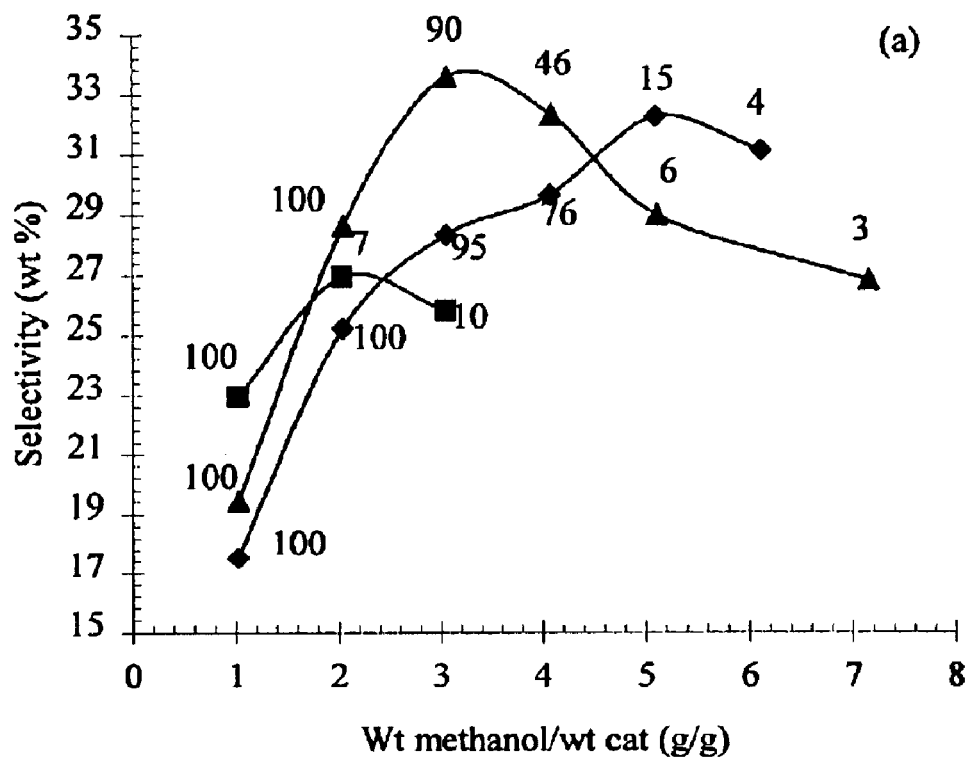
FIG. 4a shows the ethylene selectivity of boron-treated SAPO-56 as a function of the time-on-stream in a methanol to olefins conversion process.
Figure 4B:
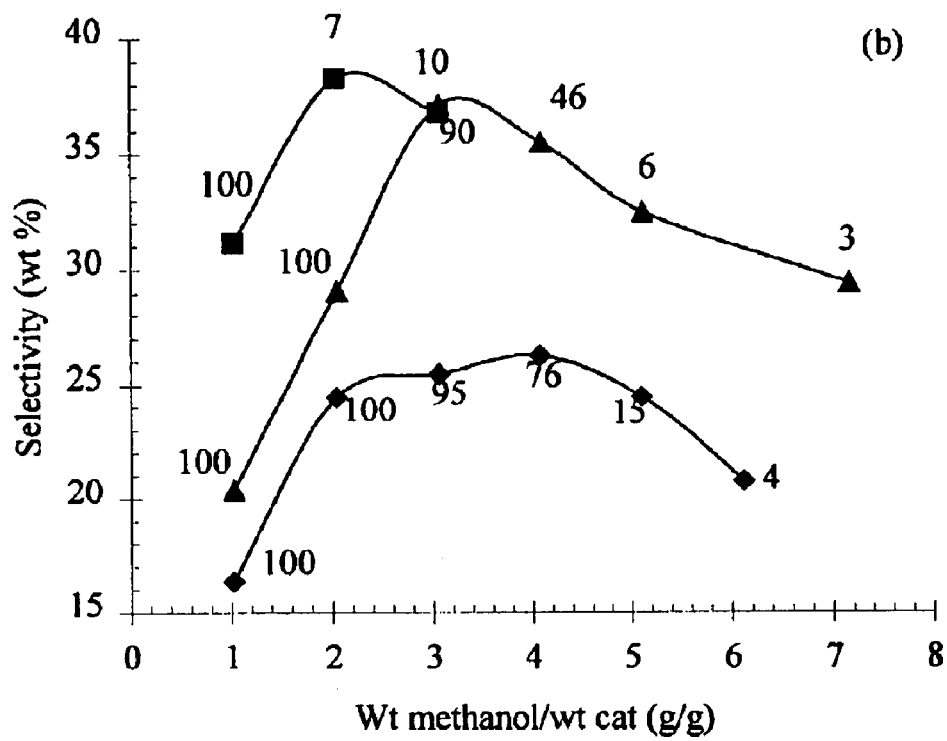
FIG. 4b shows the propylene selectivity of boron-treated SAPO-56 as a function of the time-on-stream in a methanol to olefins conversion process.

The ethylene and propylene selectivity of SAPO-56 as a function of the time-on-stream are given in FIGS. 4a and 4b. More specifically, these Figures show the ethylene (FIG. 4a) and propylene (FIG. 4b) selectivity as a function of the time on stream for SAPO-56 (filled squares), SAPO-56 loaded with 1.25 mmoles of diborane per gram of SAPO-56 (filled triangles) and SAPO-56 loaded with 3.7 mmoles of diborane per gram of SAPO-56 (filled diamonds). The numbers next to the data points indicate the conversion. FIGS. 4a and 4b show that the light olefin selectivities greatly improve after the boron treatment. Not only higher selectivities at comparable conversion levels are obtained, also the initial light olefin selectivities strongly improve, mainly at the expense of the propane and $C_4^+$ selectivity. The performance results are also given in Table 1.

5.2 SAPO-11, SAPO-17 AND SAPO-34

Several SAPO-11, SAPO-17 and SAPO-34 samples were treated with diborane ($B_2H_6$) according to the method of examples 4.1 and 2.1, respectively and were tested for their catalytic performances in the conversion of methanol to olefins, using the procedure of example 6.1. The performance results are given in Table 1.

TABLE 1

Catalytic performance of boron-treated SAPO-11, SAPO-17, SAPO-34 and SAPO-56.

| $B_2H_6$ content | $CH_4$ | $C_2^-$ | $C_2^0$ | $C_3^-$ | $C_3^0$ | $C_4^+$ | Lifetime * |
|---|---|---|---|---|---|---|---|
| SAPO-11 | | | | | | | |
| 0 | 2.35 | 2.67 | 0.23 | 5.73 | 2.38 | 86.63 | 1.78 |
| 0.29 | 2.35 | 5.57 | 0.54 | 10.97 | 5.82 | 73.83 | 0.68 |
| 0.86 | 3.27 | 5.24 | 0.57 | 12.37 | 7.01 | 70.67 | 0.67 |
| 1.28 | 4.13 | 5.26 | 0.58 | 9.74 | 5.46 | 74.42 | 0.12 |
| SAPO-17 | | | | | | | |
| 0 | 1.6 | 26.2 | 0.4 | 34.0 | 1.1 | 36.7 | N/A |
| 0.36 | 2.1 | 26.3 | 0.4 | 34.1 | 1.2 | 36.0 | N/A |
| 0.70 | 1.8 | 22.8 | 0.4 | 34.1 | 1.1 | 39.8 | N/A |
| SAPO-34 | | | | | | | |
| 0 | 0.9 | 32.2 | 0.8 | 41.7 | 3.1 | 21.2 | 12.62 |
| 0.36 | 1.2 | 32.2 | 0.9 | 40.9 | 3.3 | 21.5 | 10.59 |
| 0.58 | 1.2 | 32.4 | 0.8 | 40.3 | 2.4 | 22.9 | 10.63 |
| 0.66 | 0.9 | 32.9 | 0.9 | 41.5 | 3.6 | 20.2 | 12.5 |
| 0.70 | 1.3 | 33.1 | 0.8 | 39.8 | 3.2 | 21.7 | 10.51 |
| 0.73 | 0.8 | 33.2 | 0.8 | 40.8 | 3.0 | 21.4 | 13.14 |
| 1.16 | 0.8 | 26.2 | 0.7 | 41.0 | 4.5 | 26.8 | 8.99 |
| SAPO-56 | | | | | | | |
| 0 | 10 | 25.3 | 1.8 | 22.8 | 19.3 | 20.6 | 3.36 |
| 0.68 | 5.9 | 26.5 | 1.6 | 26.8 | 18.8 | 20.3 | 2.59 |
| 1.25 | 5.2 | 28.0 | 1.4 | 29.9 | 15.5 | 20.0 | 2.91 |
| 2.04 | 2.9 | 26.8 | 1.0 | 30.7 | 17.7 | 20.7 | 1.5 |
| 3.67 | 2.1 | 23.3 | 1.0 | 31.9 | 13.6 | 28.2 | 0.58 |

*N/A means data not available

The results in Table 1 show that treatment of the molecular sieves results in a significant increase in ethylene and propylene selectivity, mainly at the expense of the propane and $C_4^+$ selectivity.

While the present invention has been described and illustrated by reference to particular embodiments, those of ordinary skill in the art will appreciate that the invention lends itself to variations not necessarily illustrated herein.

For example, it is also contemplated the molecular sieves described herein are useful as absorbents, adsorbents, gas separators, detergents, water purifiers, and in other various uses in various areas such as agriculture and horticulture.

What is claimed is:

1. A hydrocarbon conversion process comprising the steps of:
    (a) introducing a feedatock to a reactor system in the presence of a microcrystalline metalloaluminophosphate molecular sieve having the AFX framework type and comprising within its cages and/or channels a compound containing at least one M-O group, wherein the compound containing at least one M-O group was formed by introducing a compound containing at least one M-X group within the cages of said microporous molecular sieve, wherein M is boron and X is halogen and the compound containing at least one M-O group occupies up to 50% of the volume of the cages and channels of the molecular sieve;
    (b) withdrawing from the reactor system an effluent stream; and
    (c) passing the effluent gas through a recovery system recovering at least the one or more conversion products.

2. The process of claim 1, wherein the feedstock contains at least one oxygenated hydrocarbon.

3. The process of claim 2, wherein the effluent stream contains ethylene and/or propylene.

4. The process of claim 1, wherein the modified catalyst is recycled in the hydrocarbon conversion process.

5. A process for making olefins from an oxygenate feedstock comprising the steps of
    a) providing a metalloaluminophosphate molecular sieve;
    b) introducing a compound containing at least one M-X group within the cages of said microporous molecular sieve;
    c) reacting said compound containing at least one M-X group with the acid groups located in the cages of the molecular sieve, wherein the compound containing at least one M-X group is selected from the group consisting of compounds of formula $MX_3$, compounds of fonnula $M_2X_6$, and mixtures thereof, M being boron, and each X independently being a hydrogen or halogen atom;
    d) restoring at least a portion of the acid groups located in the cages of the molecular sieve by submitting the molecular sieve to a thermal treatment;
    e) contacting the molecular sieve obtained at step d) with the oxygenate feedatock;
    f) recovering an olefin product.

6. The process of claim 5, wherein X is halogen.

* * * * *